(12) United States Patent
Lavery et al.

(10) Patent No.: US 11,094,322 B2
(45) Date of Patent: Aug. 17, 2021

(54) OPTIMIZING SPEECH TO TEXT CONVERSION AND TEXT SUMMARIZATION USING A MEDICAL PROVIDER WORKFLOW MODEL

(71) Applicant: International Business Machines Corporation, Armonk, NY (US)

(72) Inventors: Andrew J. Lavery, Austin, TX (US); Kenney Ng, Arlington, MA (US); Michael Picheny, White Plains, NY (US); Paul C. Tang, Los Altos, CA (US)

(73) Assignee: International Business Machines Corporation, Armonk, NY (US)

( * ) Notice: Subject to any disclaimer, the term of this patent is extended or adjusted under 35 U.S.C. 154(b) by 140 days.

(21) Appl. No.: 16/269,795

(22) Filed: Feb. 7, 2019

(65) Prior Publication Data

US 2020/0258510 A1     Aug. 13, 2020

(51) Int. Cl.
*G10L 15/22* (2006.01)
*G10L 15/06* (2013.01)
(Continued)

(52) U.S. Cl.
CPC ............ *G10L 15/22* (2013.01); *G10L 15/063* (2013.01); *G10L 15/183* (2013.01); *G10L 2015/088* (2013.01); *G10L 2015/223* (2013.01)

(58) Field of Classification Search
CPC ....... G06F 40/40; G10L 15/22; G10L 15/063; G10L 15/183; G10L 2015/088; G10L 2015/223
(Continued)

(56) References Cited

U.S. PATENT DOCUMENTS 7,584,103 B2   9/2009   Fritsch et al.
9,710,431 B2   7/2017   Riskin et al.
(Continued)

OTHER PUBLICATIONS

G. Suciu, R. A. Dobre, C. Butca, V. Suciu, I. Mihaila and R. Cheveresan, "Search based applications for speech processing," 2016 8th International Conference on Electronics, Computers and Artificial Intelligence (ECAI), Ploiesti, 2016, pp. 1-6, doi: 10.1109/ECAI.2016.7861101. (Year: 2016).*

(Continued)

*Primary Examiner* — Bharatkumar S Shah
(74) *Attorney, Agent, or Firm* — Reza Sarbakhsh; Edell, Shapiro & Finnan, LLC

(57) ABSTRACT

A method, a system, and a computer program product are provided. Speech signals from a medical conversation between a medical provider and a patient are converted to text based on a first domain model associated with a medical scenario. The first domain model is selected from multiple domain models associated with a workflow of the medical provider. One or more triggers are detected, each of which indicates a respective change in the medical scenario. A corresponding second domain model is applied to the medical conversation to more accurately convert the speech signals to text in response to each of the detected one or more triggers. The corresponding second domain model is associated with a respective change in the medical scenario of the workflow of the medical provider. A clinical note is provided based on the text produced by converting the speech signals.

20 Claims, 5 Drawing Sheets

(51) Int. Cl.
*G10L 15/183* (2013.01)
*G10L 15/08* (2006.01)

(58) Field of Classification Search
USPC ............................................ 704/235
See application file for complete search history.

(56) References Cited

U.S. PATENT DOCUMENTS

| | | | |
|---|---|---|---|
| 2006/0041428 A1* | 2/2006 | Fritsch | G10L 15/1815 704/257 |
| 2013/0339030 A1* | 12/2013 | Ehsani | G10L 17/00 704/275 |
| 2015/0294089 A1* | 10/2015 | Nichols | G06Q 50/22 705/3 |
| 2016/0147971 A1 | 5/2016 | Kolowitz et al. | |
| 2016/0350280 A1 | 12/2016 | Lavallee et al. | |
| 2018/0150605 A1* | 5/2018 | Co | G10L 15/1822 |
| 2018/0240538 A1 | 8/2018 | Koll et al. | |
| 2018/0275956 A1* | 9/2018 | Reed | H04R 25/554 |

OTHER PUBLICATIONS

W. Yao, J. Rolia, S. Basu, S. Singhal and A. Kumar, "A Context-Aware framework for patient Navigation and Engagement (CANE)," 8th International Conference on Collaborative Computing: Networking, Applications and Worksharing (CollaborateCom), Pittsburgh, PA, USA, 2012, pp. 316-325. (Year: 2012).*

A. Corradi, M. Destro, L. Foschini, S. Kotoulas, V. Lopez and R. Montanari, "Mobile Cloud Support for Semantic-Enriched Speech Recognition in Social Care," in IEEE Transactions on Cloud Computing, vol. 7, No. 1, pp. 259-272, Jan. 1-Mar. 2019, doi: 10.1109/TCC.2016.2570757. (Year: 2016).*

G. Suciu, R. A. Dobre, C. Butca, V. Suciu, I. Mihailaand R. Cheveresan, "Search based applications for speech processing," 2016 8th International Conference on Electronics, Computers and Artificial Intelligence (ECAI), Ploiesti, 2016, pp. 1-6, doi: 10.1109/ECAI.2016.7861101. (Year: 2016) (Year: 2016).*

Kumar et al., "Mediscript—Mobile Cloud Collaborative Speech Recognition Framework," International Conference on Innovation in Communication, Information and Computing (ICICIC) 2013, International Journal of Computer Applications (0975-8887), 2013, pp. 36-45.

Nuance, "Dragon Medical Speech Solutions for Clinicians," Nuance—Best Medical Dictation and Clinical Documentation Software, p. 1-6, Nuance Communications Inc., https://www.nuance.com/healthcare/physician-and-clinical-speech/dragon-medical.html. Accessed on Feb. 7, 2019.

MModal, "Closing the Loop in Clinical Documentation," p. 1-3, MModal IP LLC, https://mmodal.com/, Accessed on Feb. 7, 2019.

* cited by examiner

SUBJECTIVE

Patient is a 37 year old male complaining of lack of energy.
Patient recovered from suspected flu virus about 6 weeks ago.
Family history includes heart disease.
No sleep problems reported.
No other symptoms reported.

OBJECTIVE

Temperature is 99.2 degrees.
Heart rate is 80.
BP is 117/20.
Lungs are clear.
Reflexes normal.

ASSESSMENT

Possible diagnoses are: mononucelosis, low iron, heart disease.

PLAN

Diagnostic blood tests ordered.
Recommended patient get plenty of rest.
Patient to make appointment for next week to discuss blood test results and future treatment.

FIG.5

OPTIMIZING SPEECH TO TEXT CONVERSION AND TEXT SUMMARIZATION USING A MEDICAL PROVIDER WORKFLOW MODEL

BACKGROUND

1. Technical Field

Present invention embodiments relate to recognizing triggers in a medical provider's conversation to transition a speech-to-text system to an appropriate domain model optimized for speech recognition of a current portion of a workflow, and to summarize the conversation as a clinical note.

2. Discussion of the Related Art

Accurate speech-to-text processing of a live or recorded conversation between a medical provider and a patient can be very challenging. Attempts have been made to use speech-to-text processing of live or recorded conversations between medical providers and patients in order to transcribe such conversations, but such processing is not accurate enough for conversational medical transcription due to a large vocabulary and a vast combination of words that may be included in a medical conversation.

Currently, a best way for a medical provider to obtain an accurate transcription of a conversation with a patient is to record the conversation and hire a person to listen to the recording and manually transcribe the conversation. However, this approach can be very expensive.

SUMMARY

According to one embodiment of the present invention, a method of processing a medical conversation is provided. A processor converts to text speech signals from the medical conversation between a medical provider and a patient for a medical scenario based on a first domain model associated with the medical scenario. The first domain model is selected from multiple domain models, each of which is associated with a corresponding medical scenario of a workflow of the medical provider. The processor detects one or more triggers, each of which indicates a respective change in the medical scenario. The processor applies a corresponding second domain model to the medical conversation to more accurately convert the speech signals from the medical conversation to text in response to each of the detected one or more triggers. The corresponding second domain model is associated with a respective change in the medical scenario of the workflow of the medical provider. The processor provides a clinical note based on the text produced by the converting of the speech signals.

According to a second embodiment, a system for processing a medical conversation is provided. The system includes at least one processor and at least one memory connected to the at least one processor. The at least one processor is configured to perform a number of steps. According to the steps, speech signals from a medical conversation between a medical provider and a patient for a medical scenario are converted to text based on a first domain model associated with the medical scenario. The first domain model is selected from a number of domain models, each of which is associated with a corresponding medical scenario of a workflow of the medical provider. One or more triggers are detected indicating a respective change in the medical scenario. A corresponding second domain model is applied to the medical conversation to more accurately convert the speech signals from the medical conversation to text in response to each of the detected one or more triggers. The corresponding second domain model is associated with a respective change in the medical scenario of the workflow of the medical provider. A clinical note is provided based on the text produced by converting the speech signals.

According to a third embodiment, a computer program product for processing a medical conversation is provided. The computer program product includes at least one computer readable storage medium having computer readable program code embodied therewith for execution on at least one processor of a computing device. The computer readable program code is configured to perform a number of steps. According to the steps, speech signals from a conversation between a medical provider and a patient for a medical scenario are converted to text based on a first domain model associated with the medical scenario. The first domain model is selected from a number of domain models, each of which is associated with a corresponding medical scenario of a workflow of the medical provider. One or more triggers are detected, each of which indicates a respective change in the medical scenario. A corresponding second domain model is applied to the medical conversation to more accurately convert the speech signals from the medical conversation to text in response to each of the detected one or more triggers. The corresponding second domain model is associated with a respective change in the medical scenario of the workflow of the medical provider. A clinical note is provided based on the text produced by converting the speech signals.

BRIEF DESCRIPTION OF THE DRAWINGS

Generally, like reference numerals in the various figures are utilized to designate like components.

FIG. 5 shows an example clinical note that may be produced, according to some embodiments, in a subjective, objective, assessment, and planning format.

DETAILED DESCRIPTION

A domain model includes words that may be recognized when processing speech. The domain model also may include probabilities regarding words that may follow one or more recognized words. Domain models may be trained to recognize words and phrases related to different subject matter such as, for example, medicine, law, information technology, etc. in order to improve speech recognition accuracy of speech related to the different subject matter.

An office visit workflow, or workflow model, of a medical provider is an orchestrated and repeatable pattern that the medical provider uses to conduct an office visit with a patient. The medical provider may have specific office visit workflow models that are followed for different types of patient office visits. In the various office visit workflow models one or more domain models may be used to recognize and convert speech to text regarding a medical conversation between the medical provider and a patient. If a specific office visit model workflow that is being used for an office visit is known, or can be determined, then a speech-to-text system may detect when the medical conversation is transitioning to a different medical scenario for the office visit based on words or phrases recognized in the medical conversation, or via other methods. Upon detection of such a transition, the speech-to-text system may change a current domain model to another domain model that is more appropriate for accurate speech recognition during the different medical scenario.

According to various embodiments, a number of domain models may be provided for speech-to-text processing of a medical conversation in which a number of different medical scenarios can occur according to an office visit workflow model used by a medical provider for a patient's office visit. Upon recognizing, in the medical conversation, certain triggers that signal a change to a different medical scenario, the speech-to-text processing may change a current domain model to a domain model associated with the recognized trigger in order to optimize the speech-to-text processing. Each of the domain models may be associated with a respective medical scenario associated with an office visit workflow model of the medical provider and may include words, phrases and combinations of words that may be used in the conversation during the respective medical scenario. The domain models may be trained on a computing device such as, for example, server 106 or another computing device using previous interactions between respective medical providers and their respective patients.

After completion of the speech-to-text processing, the text may be summarized in a form of a clinical note, which may be provided to the medical provider.

Figure 1:
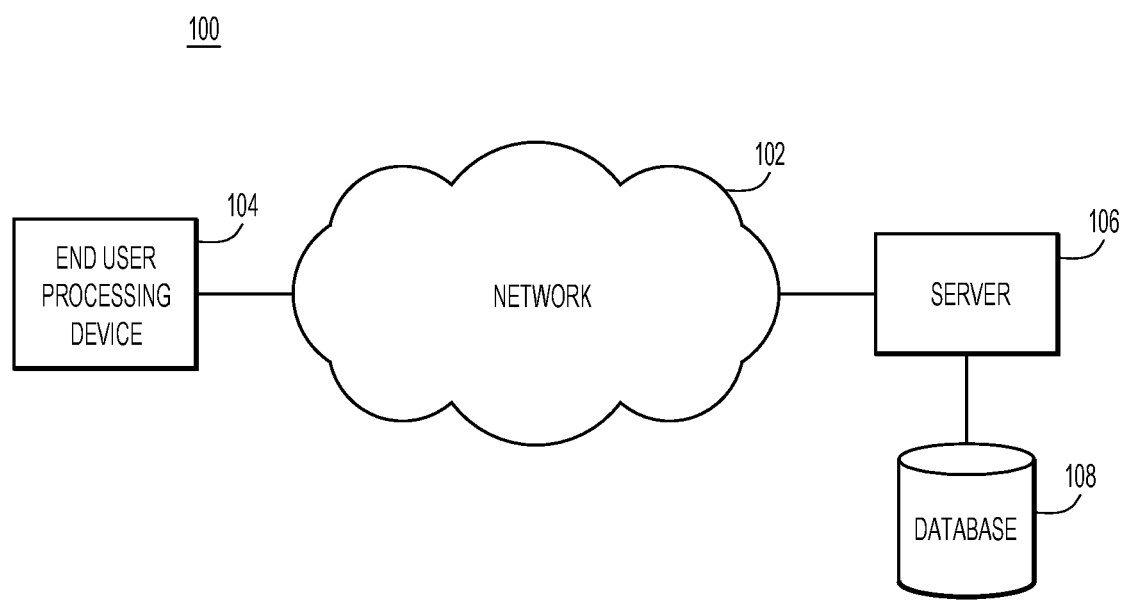
FIG. 1 shows an example operating environment according to embodiments of the invention.

An example environment 100 for use with present invention embodiments is illustrated in FIG. 1. Specifically, environment 100 may include one or more end user processing devices 104 and a server 106 connected to a network 102 either via a wired or a wireless connection. Server 106 further may be connected to a database 108, which may include domain models for speech-to-text processing during associated portions of a workflow of a medical provider. In some embodiments, server 106 may include a server farm.

In some embodiments, instead of being connected to server 106, database 108 may be connected with a database server (not shown), which further may be connected to network 102.

End user processing device(s) 104 and server 106 may be remotely located from each other and may communicate via network 102. Network 102 may be implemented by any number of any suitable communications media (e.g., wide area network (WAN), local area network (LAN), Internet, Intranet, etc.). Alternatively, end user processing device(s) 104 and server 106 may be local to each other, and may communicate via any appropriate local communication medium (e.g., local area network (LAN), hardwire, wireless link, Intranet, etc.).

In some embodiments, end user processing device 104 may receive live or recorded speech of a conversation between a medical provider and a patient and may provide speech signals from the received speech to server 106 via network 102. Either end user processing device 104 or server 106 may store the speech signals in a storage medium. Server 106 may perform speech-to-text processing of the received speech signals, using the one or more domain models, which may be stored in database 108, and that are appropriate to respective medical scenarios of an office visit workflow model, to convert the speech signals to text. Upon completion of the speech-to-text processing, server 106 may summarize the conversation in a form of a clinical note and may provide the clinical note to end-user processing device 104, from which the medical provider may confirm accuracy of the clinical note and may edit the clinical note as needed.

In an alternative embodiment, end user processing device 104 may perform speech-to-text processing of a live or recorded conversation between a medical provider and a patient and may access the domain models appropriate to different portions of the conversation via database 108 either directly or via network 102. End user processing device 104 may then summarize the conversation in a form of a clinical note and may provide a user with an opportunity to confirm accuracy of the clinical note and edit the clinical note as needed.

End user processing device(s) 104 may be a handheld computing device, a tablet computer, a smartphone, a laptop computing device, a desktop computing device, or other type of computing device.

Server 106 may include a laptop computing device, a desktop computing device, a tablet computing device, or other type of computing device.

Figure 2:
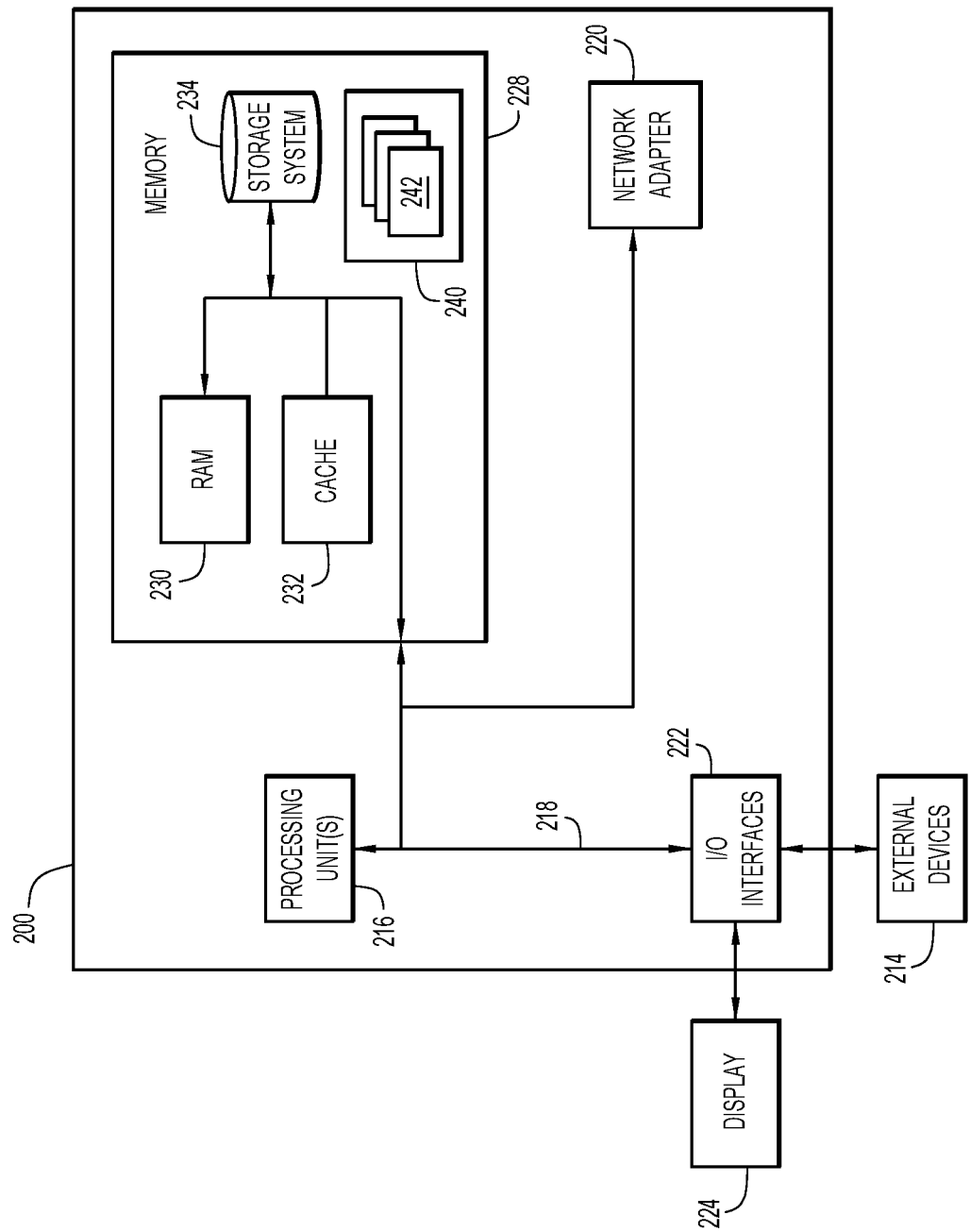
FIG. 2 shows an example computer system that may implement embodiments of the invention.

Referring now to FIG. 2, a schematic of an example computer system 200 is shown, which may implement end user processing device 104 or server 106 in various embodiments. Computer system 200 is shown in a form of a general-purpose computing device. Components of computer system 200 may include, but are not limited to, one or more processors or processing units 216, a system memory 228, and a bus 218 that couples various system components including system memory 228 to one or more processing units 216.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 200 may include a variety of computer system readable media. Such media may be any available media that is accessible by computer system 200, and may include both volatile and non-volatile media, removable and non-removable media.

System memory 228 can include computer system readable media in the form of volatile memory, such as random access memory (RAM) 230 and/or cache memory 232.

Computer system 200 may further include other removable/non-removable, volatile/non-volatile computer system storage media. By way of example only, storage system 234 can be provided for reading from and writing to a non-removable, non-volatile magnetic medium (not shown, which may include a "hard drive" or a Secure Digital (SD) card). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 228 may include at least one program product having a set (e.g., at least one) of program modules that are configured to carry out the functions of embodiments of the invention.

Program/utility 240, having a set (at least one) of program modules 242, may be stored in memory 228 by way of example, and not limitation, as well as an operating system, one or more application programs, other program modules, and program data. Each of the operating system, the one or more application programs, the other program modules, and the program data or some combination thereof, may include an implementation of a networking environment. Program modules 242 generally carry out the functions and/or methodologies of embodiments of the invention as described herein.

Computer system 200 may also communicate with one or more external devices 214 such as a keyboard, a pointing device, one or more displays 224, one or more devices that enable a user to interact with computer system 200, and/or any devices (e.g., network card, modem, etc.) that enable computer system 200 to communicate with one or more other computing devices. Such communication can occur via Input/Output (I/O) interfaces 222. Still yet, computer system 200 can communicate with one or more networks such as a local area network (LAN), a general wide area network (WAN), and/or a public network (e.g., the Internet) via network adapter 220. As depicted, network adapter 220 communicates with the other components of computer system 200 via bus 218. It should be understood that, although not shown, other hardware and/or software components could be used in conjunction with computer system 200. Examples, include, but are not limited to: a microphone, one or more speakers, microcode, device drivers, redundant processing units, external disk drive arrays, RAID systems, tape drives, and data archival storage systems, etc.

Figure 3:
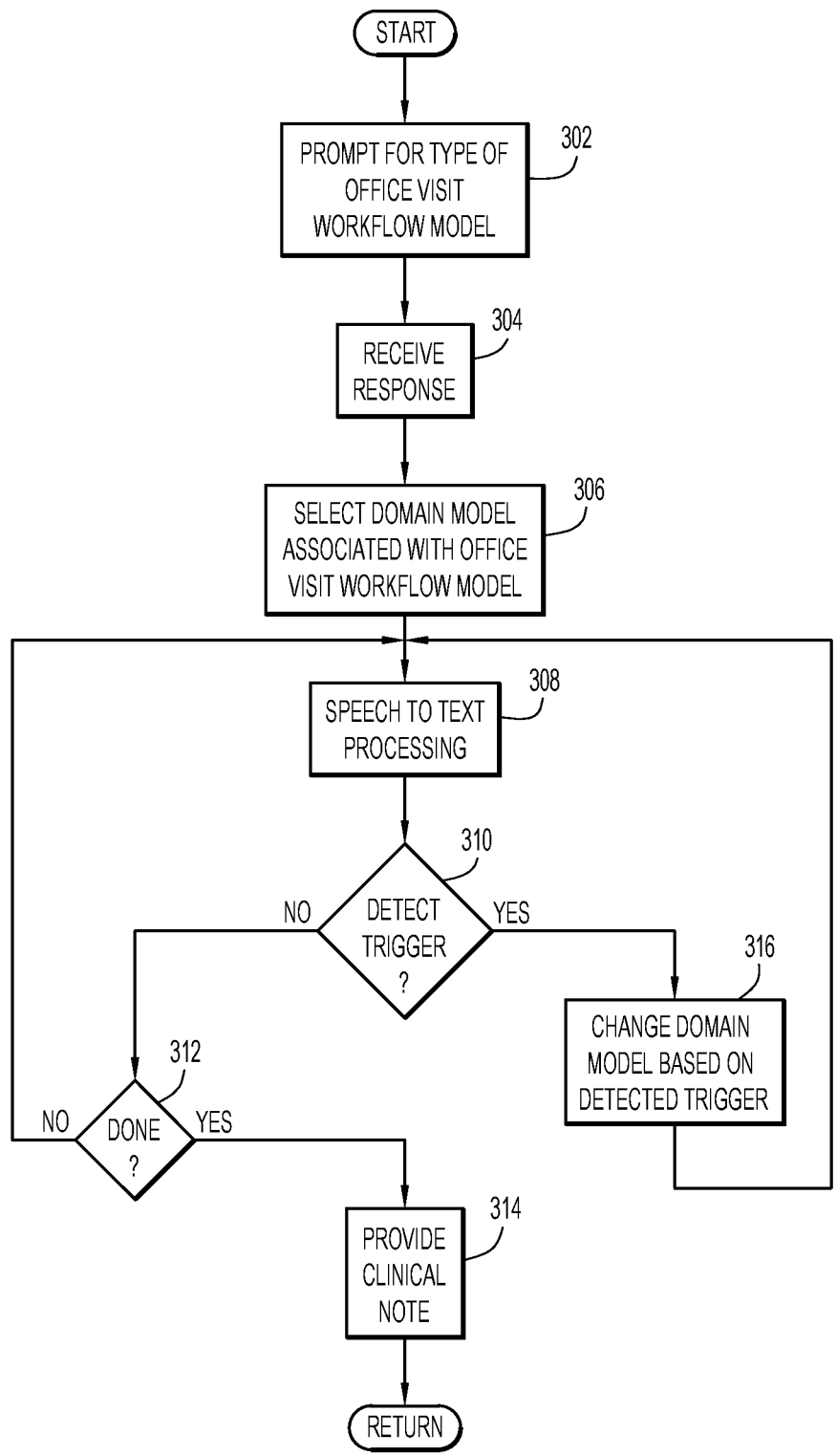
FIG. 3 is a flowchart of an example process for converting speech of a medical conversation to text according to embodiments of the invention.

FIG. 3 is a flowchart that illustrates an example process that may be performed in a computing device such as, for example, end user processing device 104, server 106, or a combination thereof according to embodiments of the invention. The process may begin by prompting a user, who may be a medical provider, to provide a type of office visit workflow model (act 302). During act 304, the computing device may receive a response from the user including the type of the office visit workflow model. As a result, a domain model corresponding to a medical scenario of the office visit workflow model may be selected for use (act 306).

In an alternative embodiment, instead of the user being prompted for the type of office visit workflow model, the computing device may access a schedule of the user, or medical provider, and may determine the type of office visit workflow model based on a time of day and the schedule and may select a corresponding domain model for an office visit workflow model corresponding to an office visit type on the schedule.

The process may then proceed to perform speech-to-text processing of live or recorded speech (act 308). During the speech-to-text processing, the computing device may determine whether one of a number of possible triggers is detected (act 310).

In some embodiments, the computing device may be trained to recognize certain words and/or phrases as signaling a transition in a medical scenario of the office visit workflow model. In other embodiments, the words and/or phrases selected as the triggers may be a result of training the computing device to determine words or phrases used in a medical conversation as a change in the medical scenario occurs. The triggers may include statements such as, for example, "let's begin your physical exam", "what seems to be bothering you today", "I would like to listen to your heart", "let's begin with your family medical history", etc. If a trigger is detected, then the computing device may change the domain model to an appropriate domain model for recognizing speech corresponding to the changed medical scenario of the office visit workflow model (act 316). Acts 312-316 may again be performed.

In some embodiments, other techniques may be used for detecting a trigger to cause a change in a current domain model corresponding to a change in a medical scenario of the office visit workflow model. For example, medical equipment including, but not limited to, a stethoscope and/or an otoscope, may include one or more sensors to detect use by a medical provider. When one or more of the sensors detects the use of either the stethoscope or the otoscope, the one or more of the sensors may send a signal, which can act as a trigger indicating a transition to another medical scenario of the office visit workflow model, which may further cause a corresponding change in a current domain model to optimize speech recognition.

If, during act 310, no trigger is detected, then a determination may be made regarding whether the medical conversation has ended (act 312). In some embodiments, the ending of the medical conversation may be determined based on detecting certain words or phrases spoken by the user such as, for example, "the end" or other words or phrases. In other embodiments, the end of the conversation may be determined by the computing device recognizing a selection of a button or an indicator displayed on a touch screen, or via other methods. If the end of the medical conversation is detected, then the computing device may provide a summary of the medical conversation as a clinical note (act 314).

Figure 4:
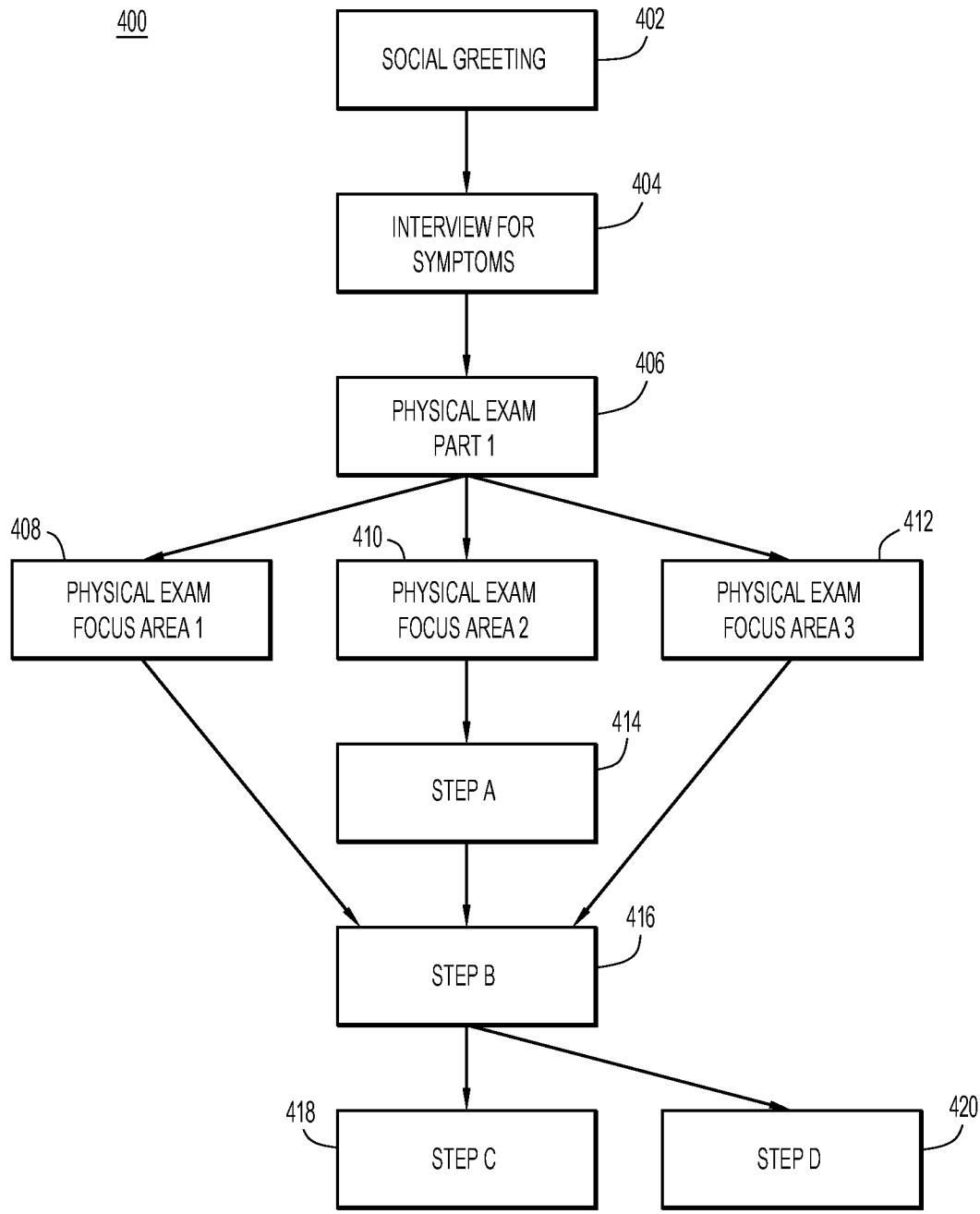
FIG. 4 illustrates an example workflow model according to embodiments of the invention.

FIG. 4 illustrates an example medical provider's office visit workflow model 400 for a pediatric sick child visit. The office visit workflow model may start with a medical provider giving a social greeting 402 to say hello to a patient and family members. The medical provider then may interview the patient regarding his or her symptoms 404. The interview may be followed by a set of physical exam steps that may hone in on certain focus areas, depending on findings from earlier steps 408-420. A respective domain model may be trained for each step of the office visit workflow model. In such an embodiment, when a trigger is detected signaling a change to a different medical scenario of the office visit workflow model, a current domain model may be changed to a domain model appropriate for the different medical scenario.

Alternatively, some domain models may be trained to cover multiple steps of the office visit model, while other domain models may be trained to cover respective single steps of the office visit model. For example, respective single domain models may be trained for steps 402 and 404 of the office visit model, a second domain model may be trained for step 406 of the office visit model, a third domain model may be trained for steps 410 and 414 of the office visit model, fourth and fifth domain models may be trained, respectively, for step 408 and step 412, and separate respective domain models may be trained for steps 416, 418 and 420.

Various embodiments may include a number of different domain models, for use with a number of different office visit workflow models. For example, some embodiments may have domain models for an annual adult physical office visit workflow model, an adult sick office visit workflow model, a well-baby office visit workflow model, etc. Some domain models could be less specific, or more granular, versions of other domain models such as, for example, a domain model for a medical scenario of a sick office visit workflow model may be more granular than a domain model associated with a different medical scenario of the sick office visit workflow model related to a particular type of illness or a particular set of symptoms. In such embodiments, triggers may indicate a change of the current domain model.

In various embodiments, a clinical note may be produced based on text produced by recognizing speech of a medical conversation between a medical provider and a patient. The clinical note may summarize important aspects of the office visit. In some embodiments, the clinical note may be produced in one of a number of different formats. For example, some embodiments may produce the clinical note in a subjective, objective, assessment, and planning (SOAP) format, while other embodiments may produce the clinical note in another format.

Any of a number of methods exist for performing text summarization in various embodiments. Two main approaches are extractive methods and abstractive methods. Extractive methods identify and extract important sections of text and generate them word for word. Abstractive methods examine and interpret the text using advanced natural language processing techniques to generate a shorter version of the text that conveys important information from the original text. Either of these methods or other methods may be used in various embodiments to summarize the clinical note.

FIG. 5 shows an example clinical note in the SOAP format, which may be generated from a medical conversation converted from speech to text. In FIG. 5, the subjective portion of the critical note includes information reported by the patient. The objective portion of the critical note includes information that a medical provider can observe or measure. The assessment portion of the critical note includes possible diagnoses usually in an order from most likely to least likely. The planning portion of the critical note includes, but is not limited to, information about any lab tests ordered, recommendations for the patient, future treatment, etc.

A classifier, which may be trained to analyze text and classify portions of text according to a format to be used to produce a clinical note, may be included in some embodiments. Each of the portions of text classified as belonging to a same respective portion of the clinical note format may be analyzed together to produce a summary for that same respective portion of the clinical note format using extractive, abstractive, or other methods to summarize each of the respective portions of the clinical note. For example, in embodiments that produce a clinical note in the SOAP format, respective portions of the classified text associated with a same respective classification may analyzed together to produce a summary including a subjective portion based on portions of the text classified as belonging to a subjective portion of the SOAP format, an objective portion based on portions of the text classified as belonging to an objective portion of the SOAP format, an assessment portion based on portions of the text classified as belonging to the assessment portion of the SOAP format, and a planning portion based on portions of the text classified as belonging to the planning portion of the SOAP format.

In some of the embodiments, the computing device may automatically perform actions based on the clinical note. For example, if the clinical note indicates that diagnostic tests are to be ordered, the computing device may automatically generate a referral to a provider of the diagnostic tests. Similarly, if the clinical note indicates that a script for a prescription drug is to be provided to a patient, the computing device may contact a pharmacy to prepare the prescription drug for the patient. Further, some embodiments may access a patient's profile to determine a patient's preferred pharmacy to which a script may be automatically sent, and may access the patient's profile to determine a patient's preferred lab to which a referral for lab tests may automatically be generated for the patient.

It will be appreciated that the embodiments described above and illustrated in the drawings represent only a few of the many ways of implementing the various embodiments.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, etc.). These systems may include any types of monitors and input devices (e.g., keyboard, mouse, voice recognition, etc.) to enter and/or view information.

It is to be understood that the software of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments may be available on a non-transitory computer useable medium (e.g., magnetic or optical media, magneto-optic media, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., knowledge base, units of work, action graphs, critical path graphs, etc.). The database system may be implemented by any number of any conventional or other databases, data stores or storage structures to store information. The database system may be included within or coupled to a server and/or client systems. The database systems and/or storage structures may be remote from or local to the computer or other processing systems, and may store any desired data.

The present invention embodiments may employ any number of any type of user interface (e.g., Graphical User Interface (GUI), command-line, prompt, etc.) for obtaining or providing information, where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A method of processing a medical conversation comprising:
converting to text, via a processor, speech signals from the medical conversation between a medical provider and a patient for a workflow of the medical provider based on a first domain model of a plurality of domain models, wherein the workflow includes a plurality of medical scenarios and the plurality of domain models are each trained for a corresponding medical scenario of the workflow, and wherein the first domain model is associated with a current medical scenario of the medical conversation;
detecting, via the processor during the converting to text, one or more triggers occurring during the medical conversation, each of the one or more triggers indicating a change to a different medical scenario of the workflow within the medical conversation;
in response to each of the detected one or more triggers, applying, via the processor during the converting to text, a corresponding second domain model of the plurality of domain models to the speech signals of the medical conversation pertaining to the different medical scenario indicated by the detected trigger to convert the speech signals pertaining to the different medical scenario indicated by the detected trigger from the medical conversation to text, wherein the corresponding second domain model is trained for the different medical scenario indicated by the detected trigger; and
providing, via the processor, a clinical note based on the text produced from the speech signals of the medical conversation.

2. The method of claim 1, further comprising storing the speech signals from the medical conversation, wherein the applying the corresponding second domain model further comprises:
applying a plurality of second domain models to the stored speech signals based on the detected one or more triggers to convert the stored speech signals to text.

3. The method of claim 2, wherein
the detecting of the one or more triggers is based on recognizing at least one of certain words, certain phrases and certain combinations of words in the medical conversation.

4. The method of claim 1, further comprising:
learning, via the processor, one or more domain models based on previous interactions between a medical provider and a patient.

5. The method of claim 1, wherein the plurality of domain models includes domain models at different levels of granularity for corresponding medical scenarios.

6. The method of claim 1, wherein the plurality of domain models includes a domain model for use with a plurality of different medical scenarios.

7. The method of claim 1, further comprising:
automatically performing, via the processor, an action included in the clinical note.

8. A system for processing a medical conversation, the system comprising:
at least one processor; and
at least one memory connected to the at least one processor, the at least one processor being configured to:
convert to text speech signals from the medical conversation between a medical provider and a patient for a workflow of the medical provider based on a first domain model of a plurality of domain models, wherein the workflow includes a plurality of medical scenarios and the plurality of domain models are each trained for a corresponding medical scenario of the workflow, and wherein the first domain model is associated with a current medical scenario of the medical conversation;

detect, during the converting to text, one or more triggers occurring during the medical conversation, each of the one or more triggers indicating a change to a different medical scenario of the workflow within the medical conversation;

in response to each of the detected one or more triggers, apply during the converting to text a corresponding second domain model of the plurality of domain models to the speech signals of the medical conversation pertaining to the different medical scenario indicated by the detected trigger to convert the speech signals pertaining to the different medical scenario indicated by the detected trigger from the medical conversation to text, wherein the corresponding second domain model is trained for the different in the medical scenario indicated by the detected trigger; and provide a clinical note based on the text produced from the speech signals of the medical conversation.

9. The system of claim 8, wherein the at least one processer is further configured to:

store the speech signals from the medical conversation, wherein the at least one processor being configured to apply the corresponding second domain model further comprises the at least one processor being configured to:

apply a plurality of second domain models to the stored speech signals based on the detected one or more triggers to convert the stored speech signals to text.

10. The system of claim 8, wherein the detecting of the one or more triggers is based on at least one of recognizing one or more certain words in the medical conversation and receiving signals from at least one sensor associated with a medical device.

11. The system of claim 8, wherein the at least one processor is further configured to:

learn one or more domain models based on previous interactions between a medical provider and a patient.

12. The system of claim 8, wherein the plurality of domain models includes domain models at different levels of granularity for corresponding medical scenarios.

13. The system of claim 8, wherein the plurality of domain models includes a domain model for use with a plurality of different medical scenarios.

14. The system of claim 8, wherein the clinical note is arranged according to a subjective, objective, assessment and plan format.

15. A computer program product for processing a medical conversation, the computer program product comprising at least one computer readable storage medium having computer readable program code embodied therewith for execution on at least one processor of a computing device, the computer readable program code being configured to:

convert to text speech signals from the medical conversation between a medical provider and a patient for a workflow of the medical provider based on a first domain model of a plurality of domain models, wherein the workflow includes a plurality of medical scenarios and the plurality of domain models are each trained for a corresponding medical scenario of the workflow, and wherein the first domain model is associated with a current medical scenario of the medical conversation;

detect, during the converting to text, one or more triggers occurring during the medical conversation, each of the one or more triggers indicating a change to a different medical scenario of the workflow within the medical conversation;

in response to each of the detected one or more triggers, apply during the converting to text a corresponding second domain model of the plurality of domain models to the speech signals of the medical conversation pertaining to the different medical scenario indicated by the detected trigger to convert the speech signals pertaining to the different medical scenario indicated by the detected trigger from the medical conversation to text, wherein the corresponding second domain model is trained for the different medical scenario indicated by the detected trigger; and provide a clinical note based on the text produced from the speech signals of the medical conversation.

16. The computer program product of claim 15, wherein the computer readable program code is further configured to:

store the speech signals from the medical conversation, wherein the applying the corresponding second domain model further comprises:

applying a plurality of second domain models to the stored speech signals based on the detected one or more triggers to convert the stored speech signals to text.

17. The computer program product of claim 15, wherein the detecting of the one or more triggers is based on receiving signals from at least one sensor indicating use of a medical device by the medical provider.

18. The computer program product of claim 15, wherein the computer readable program code is further configured to:

learn one or more domain models based on previous interactions between a medical provider and a patient.

19. The computer program product of claim 15, wherein the plurality of domain models includes a domain model for use with a plurality of different medical scenarios.

20. The computer program product of claim 15, wherein the plurality of domain models includes domain models at different levels of granularity for corresponding medical scenarios.

* * * * *